United States Patent [19]

Cates et al.

[11] Patent Number: 5,194,723
[45] Date of Patent: Mar. 16, 1993

[54] PHOTOACOUSTIC CONTROL OF A PULSED LIGHT MATERIAL REMOVAL PROCESS

[75] Inventors: Michael C. Cates, Solana Beach; Richard R. Hamm, San Diego, both of Calif.

[73] Assignee: Maxwell Laboratories, Inc., San Diego, Calif.

[21] Appl. No.: 813,866

[22] Filed: Dec. 24, 1991

[51] Int. Cl.$^5$ .............................................. G01J 1/32
[52] U.S. Cl. .................................. 250/205; 367/135; 219/121.62
[58] Field of Search ............................. 250/205, 226; 219/121.62, 121.61, 121.69, 121.68; 73/655; 356/326, 328; 367/135, 96, 97

[56] References Cited

U.S. PATENT DOCUMENTS

| | | | |
|---|---|---|---|
| 3,700,850 | 10/1972 | Lumley et al. | 219/121 |
| 3,986,391 | 10/1976 | Vahaviolos | 219/121 |
| 4,249,956 | 2/1981 | Hartman | 134/7 |
| 4,398,961 | 8/1983 | Mason | 134/19 |
| 4,419,562 | 12/1983 | Jon et al. | 219/130 |
| 4,491,484 | 1/1985 | Williams | 134/4 |
| 4,504,727 | 3/1985 | Melcher et al. | 219/121 |
| 4,543,486 | 9/1985 | Rose | 250/492 |
| 4,588,885 | 5/1986 | Lovoi et al. | 250/226 |
| 4,682,594 | 7/1987 | Mok | 128/303 |
| 4,718,974 | 1/1988 | Minaee | 156/643 |
| 4,731,125 | 3/1988 | Carr | 134/1 |
| 4,737,628 | 4/1988 | Lovoi | 250/226 |
| 4,803,021 | 2/1989 | Werth et al. | 264/25 |
| 4,836,858 | 6/1989 | Reinhart | 134/1 |
| 4,867,796 | 9/1989 | Asmus et al. | 131/1 |
| 4,994,639 | 2/1991 | Dickinson et al. | 219/121 |
| 5,013,366 | 5/1991 | Jackson et al. | 134/1 |
| 5,024,968 | 6/1991 | Engelsberg | 437/173 |
| 5,045,669 | 9/1991 | Ortiz, Jr. et al. | 219/121.62 |

OTHER PUBLICATIONS

Klauser, H. E., "Closed-Loop Laser Control System", *IBM Technical Disclosure Bulletin*, 24(9), (Feb. 1882), pp. 4691–4692.

Yaeck, C. E., et al., "Transient Photoacoustic Monitoring of Pulse Laser Drilling", *Appl. Phys. Lett.*, 41(11), (Dec. 1, 1982), pp. 1403–1404.

Schmitz, W. N., "Xenon Flashlamp/$CO_2$ Pellet Blasting or Paint Stripping/Coatings Removal", *Proceedings of the DOD/Industry Advanced Coatings Removal Conference*, San Diego, Calif. (Apr. 30/May 2, 1991).

Cates, M. C., "Modeling of the Flashblast Coating Removal Process", *Proceedings of the DOD/Industry Advanced Coatings Removal Conference*, San Diego, Calif. (Apr. 30–May 2, 1991), pp. 1–13.

Primary Examiner—David C. Nelms
Assistant Examiner—Que T. Le
Attorney, Agent, or Firm—Fitch, Even, Tabin & Flannery

[57] ABSTRACT

The present invention provides an automated system and method for removing one or more layers of a material from a substrate. The system and method include irradiating a structure comprising at least one layer of material formed on a substrate with a light beam having an intensity sufficient to ablate the materials in order to expose selected regions of the substrate, where the ablated material generates photoacoustic signature signals; scanning the structure with the light beam along a predetermined path at a scan speed; detecting the photoacoustic signature signals; determining an updated scan speed functionally related to the detected photoacoustic signals; and directing the scan speed to be equal to the updated scan speed. Another embodiment exposes a selected layer of a multilayered structure in a process which includes irradiating the surface of multilayered structure at a first location with a light beam having sufficient intensity to ablate the irradiated layer and generate photoacoustic pressure wave signals; detecting the photoacoustic pressure wave signals generated at the irradiated surface; comparing representations of the photoacoustic pressure wave signals with a reference value corresponding to a photoacoustic signature signal of a layer of the structure selected to be exposed; and directing the light source to scan the surface of the structure at a scan speed functionally related to the difference between the photoacoustic pressure wave signals and the reference value.

33 Claims, 5 Drawing Sheets

PHOTOACOUSTIC CONTROL OF A PULSED LIGHT MATERIAL REMOVAL PROCESS

The present invention relates to a material removal system, and more particularly, to a system that directs pulsed light (radiant energy) at a material to be removed from a substrate and uses the resulting photoacoustic effect to control the amount of material removed.

BACKGROUND OF THE INVENTION

Material coatings are pervasive in our energy-intensive, consumption-oriented society. Coatings provide: immunity to corrosion, thermal insulation, shielding, as well as appearance enhancement, and an aid in identification.

During the life of many manufactured products, such as aircraft and ships, painted coatings require removal and replacement for a variety of reasons. For example, refurbishment of the paint on aircraft is a regular maintenance item. Commercial airlines repaint their aircraft about every 4-5 years of service, depending on the age and operating hours of the craft. The United States military typically repaints its aircraft after three years of service, or less.

The removal of paint from the surfaces of aircraft presents special problems, in part, due to their large and irregularly shaped surfaces. Another difficulty is that, because the surfaces of aircraft are principally lightweight aluminum or organically based composite materials, they are particularly susceptible to damage which could compromise their structural integrity.

Many different methods have been used to remove painted coatings from aircraft. One type, the "particle medium blast" (PMB) method involves impinging the surface to be stripped with particles such as BB's, steel shot, wheat, starch, and/or sand. However, this method generates unwanted dust, requires large quantities of bulk blast materials and is noisy. PMB is also difficult to control. If the impinging particles dwell too long at one location, the surface of the aircraft may become pitted or stress hardened which can change the loading on that portion of the aircraft. PMB also damages putty joints often found on aircraft between surface plates. Another major problem is when paint materials, which are generally toxic, are impinged by the blast particles, the waste produced is toxic. Toxic waste requires special handling in order to dispose of it in a manner which minimizes damage to the environment. Another problem with PMB is that it generates a lot of dust which obscures the area being stripped. This impairs visual feedback necessary to control the process, resulting in damaged surfaces.

Some airlines have used water jets to remove paint from aircraft. However, friction caused as a water jet impacts a surface such as aluminum generates heat which can damage the aluminum, especially if it is thin, like that found on aircraft. Another problem with this method is that the high pressure water can penetrate into the internal regions of the aircraft which are susceptible to water damage.

It is also known in the art to apply chemical compounds to painted surfaces in order to chemically breakdown the layers of paint, thereby stripping the paint away from the surface to be exposed. Certain of such chemical compounds have been used to remove paint from aircraft. However, such compounds may pose a risk to human health, are usually toxic, and often not biodegradable. Overall, these types of compounds are difficult and costly to dispose of because they present serious environmental problems.

Mechanical paint removal techniques have also been employed. For example, U.S. Pat. No. 4,836,858, entitled "Ultrasonic Assisted Paint Removal Method" discloses a hand held tool which uses an ultrasonic reciprocating edge placed in contact with the surface to be stripped. Unfortunately, employment of this tool is labor intensive and relies upon the skill of a human operator to use it effectively. Further, control of this tool is a problem because the aircraft surface may still be damaged if there is excessive tool dwell at one location.

Radiant energy paint removal techniques are also known in the art. One such system uses a laser and video frame grabber in a video controlled paint removal system in which paint is stripped from a surface using particle medium blast methods of the type discussed above while a video camera converts images of the surface being stripped into electronic data signals. The data signals are used to control the particle blast. A processor compares the data signals with parameters stored in a memory to determine whether sufficient paint has been removed from the surface being stripped. If an insufficient amount of paint has been removed, then the surface continues being irradiated. If the optically irradiated area has been adequately stripped, the processor directs the particles to strip another area.

A significant problem with the video controlled paint removal system is that the amount of data which is generated and which must be processed is enormous. Hence, real time control of video controlled paint removal systems is extremely difficult. Another problem with a video controlled paint removal system is that large amounts of dust are generated from the effect of the particle blast impacting the surface being stripped. The dust can impair the scene being observed by the video camera, also making real time control of the process difficult.

Thus, it can be appreciated that coating removal, and particularly, the removal of paint from large, delicate surfaces such as found on aircraft is a problem which has not yet been satisfactorily solved.

The practice of photoacoustic spectroscopy (PAS) for analyzing a given solid material is also known. In PAS, light energy is absorbed by a solid material, converted into an acoustic wave or pressure pulse which is characteristic of the solid material, and then converted into an electrical signal for analysis purposes. In such PAS systems, a laser is employed to direct light energy at the solid material, although other types of light sources may also be used. The material absorbs the light energy in a way characteristic of the particular solid material being irradiated. Any light absorbed by the material is converted, in part or in whole, to heat. An acoustic signal results from the time dependent heat flow from the solid material to the surrounding gas. The heat flow causes oscillatory time dependent pressure in a small volume of gas at the solid-gas interface. An additional source of time dependent pressure in the gas can arise when the absorbing solid ablates and subsequently burns to release its heat of combustion. It is this motion of the gas which produces the acoustic signal that is characteristic of the solid, also referred to as the photoacoustic characteristic of the solid.

The strength of the photoacoustic wave is approximated by a theory attributable to Taylor and Sedov (D.

A. Freiwald and R. A. Axford, *J. Appl. Phys.*, Vol. 46, p. 1171, 1975), which predicts the pressure behind the shock for a spherical blast wave to be:

$$P = [2/(\gamma + 1)](4/25)(\xi_0^5)(E/R^3)$$

where $\gamma$ is the heat capacity ratio for the ambient air, $\xi$ is a constant, ($\xi = 1.03$ for air), E is the energy absorbed by the surface of the material being irradiated, and R is the distance of the pressure wave from the surface. The Taylor, et al. theory predicts that the strength of the wave is directly proportional to the energy absorbed by the surface, which in turn depends on the absorptivity of the surface at the wavelength of the light source.

An example of a system which detects and measures a photoacoustically generated pressure pulse to control a material removal process is described in U.S. Pat. No. 4,504,727, "LASER DRILLING SYSTEM UTILIZING PHOTOACOUSTIC FEEDBACK." The system described in the '727 patent uses photoacoustic feedback to control laser drilling of a multilayered printed circuit board. The system analyzes the photoacoustic feedback signals by comparing the photoacoustic outputs from the different layers of the circuit board with reference signals stored in a memory, and adjusts the laser parameters such as pulse duration, wavelength, and energy output, pulse repetition rate, and the number of pulses for each successive layer accordingly. The circuit board is mounted to an X-Y moving table under the direction of the control system which positions selected hole sites on the circuit board under the laser beam. However, the system described in the '727 patent is not suitable for removing selected layers of material from large surfaces in predetermined patterns.

The types of lasers described in the '727 patent are very long wavelength devices, therefore, every surface looks black to such lasers, with little or no reflected light energy. Because of this, it would be difficult to distinguish material coatings based on their albedo. Therefore, the use of a far infrared optical energy source to ablate material from a structure likely results in generation of photoacoustic pulses that depend more on the mechanical damping properties and resonance of the structure than on the characteristics of the ablating material.

Furthermore, the system described in the '727 patent modulates the output of the light source as a function of the amplitude of the photoacoustic signals. Such modulation disadvantageously shortens the useful life of the laser.

Thus, there is great need for a system and method which can easily and inexpensively remove coatings and which does not present the environmental problems of some of the systems and methods described above. A need also exists for a coating removal system and method that can be controlled to avoid subjecting a surface which is to be exposed to an excessive amount of energy which would damage delicate structures. A further need exists for a coating removal systems which can be automated. Still further, a need exists for a system and method which promotes a long service life of the light source.

SUMMARY OF THE INVENTION

The present invention provides an automated system and method for removing material which includes (1) irradiating a structure comprising at least one layer of material formed on a substrate with a light beam having an intensity sufficient to ablate the materials in order to expose selected regions of the substrate, where the ablated material generates photoacoustic pressure wave signals; (2) scanning the structure with the light beam along a predetermined path at a scan speed; (3) detecting the photoacoustic pressure wave; (4) determining an updated scan speed functionally related to the detected photoacoustic pressure wave signals; and (5) directing the scan speed to be equal to the updated scan speed.

Another embodiment of the present invention exposes a selected layer of a multilayered structure in a process which includes (1) irradiating the surface of multilayered structure at a first location with a light beam having sufficient intensity to ablate the irradiated layer; (2) detecting photoacoustic pressure wave signals generated at the irradiated surface; (3) comparing representations of the photoacoustic pressure wave signals with a reference value corresponding to a photoacoustic pressure wave signal of a layer of the structure selected to be exposed; and (4) directing the light source to irradiate a second selected location on the structure if the result of step (3) indicates the photoacoustic pressure wave signals are within a predetermined limit of the reference value.

An advantage of the present invention is that it provides an automated system for removing coatings from a substrate. Another advantage of the invention is that it is able to remove layers of coatings without damaging the layer to be exposed. A further advantage is that the invention may be employed to expose a selected layer of a multilayered structure. The invention also overcomes noise, environmental, and material handling problems associated with prior art material removing systems. A still further advantage is that the invention may be employed to remove coatings having varying, non-uniform thicknesses. These and other advantages of the present invention will become more readily appreciated upon review of the specification, drawings, and claims.

BRIEF DESCRIPTION OF THE DRAWINGS

Throughout the specification and various views of the drawings, like components are referred to with like reference numerals.

DESCRIPTION OF THE PREFERRED EMBODIMENTS

The following description is of the best mode presently contemplated for carrying out the invention. This description is not to be taken in a limiting sense, but is made for the purpose of describing the general principles of the invention. The scope of the invention should be determined with reference to the claims.

The present invention provides an automated system and method for exposing a selected surface of a layer of material of a multilayered structure formed of two or more layers of material, as for example, two layers of paint formed on an aluminum plate. The operation of the invention relies upon the phenomenon that different types of materials generate photoacoustic pressure wave signals when they ablate, and that these signals may be distinguished and used to control the process. Ablation is the rapid decomposition and vaporization of a material resulting from the absorption of energy by the material and is associated with the generation of pressure waves radiating from the surface of the material. The intensity of the pressure waves is characteristic of the ablating material.

An example of a system and method that uses photoacoustic feedback to control a material removal process embodying various features of the present invention directs an intense light beam to irradiate the surface of a layer of material of a multilayered structure which may be formed one or more layers of material formed on substrate. The intensity of the light is sufficient to cause the irradiated surface to absorb enough light energy in the form of heat so that the material comprising the layer ablates. This generates a photoacoustic pressure wave signals characteristic of the amount of material. As this process continues, additional material from the successive layers ablate. By detecting and discriminating the photoacoustic pressure wave signals, it can be determined when a particular layer of the substrate has been exposed. The light is then directed to irradiate another region of the structure, thereby preventing damage to the substrate from excessive heat absorption. Thus, the photoacoustic pressure wave can be used to control a material removal process.

The present invention is particularly well suited for removing layers of paint and epoxy from metallic surfaces. This is because the photoacoustic pressure wave signal characteristic of bare metal is virtually non-existent. The invention may also be used to strip corrosion from metal substrates. One principal advantage of the invention is that selected layers of a structure can be exposed without regard to the thickness of any of the layers. The above applications are provided by way of example only, and are not to be construed as limiting application of the invention.

A general overview of the present invention is described with reference to FIG. 1 where there is shown pulsed light source 10 controlled by light control o circuit 11. Light source 10 generates light beam 12 which is emitted through window 13 so that it irradiates a selected region of multilayered structure 14. For purposes of illustration, structure 14 is described herein as having layers 16 and 18 formed on substrate 20, where in this example, it is desired to expose substrate 20. However, it is to be understood, that structure 14 may be comprised of any number of layers formed on a substrate to be exposed. Light source 10 provides the energy used to remove layers 16 and 18 through a process known as ablation. In typical applications of the invention, layers such as 16 and 18 are comprised of organic compounds.

An important feature of the invention is that it limits the amount of light exposure to which substrate 20 is subjected so that it is not damaged from absorbing too much energy. Damage caused by heat includes changes in the desired mechanical properties of the material, as for example, the modulus of elasticity, tensile strength, and/or shear strength. Heat damage could also cause the material to become distorted from its intended shape.

Layer 16 is ablated upon exposure to pulsed light beam 12, causing photoacoustic pressure wave signals 22 to be generated from irradiated surface 17. Pressure wave signals 22 which are detected by fast pressure transducer 24. After removal of layer 16 in the area of where light beam 12 impinges structure 14, continued irradiation results in ablation of layer 18, accompanied by generation of its own photoacoustic pressure wave signals.

During this time, light source 10 scans structure 14 in a predetermined path at a speed related to the average peak intensity of photoacoustic pressure wave signals 22. A computer controlled robotic positioning system, comprising robotic positioner 28 to which light source 10 is mounted, and robotic controller 29, is employed to move the light source along a predetermined path. Robotic positioner 28 is controlled by robotic controller 29 in accordance with instructions provided by data processor 30. Fast pressure transducer 24, also mounted to robotic positioner 28, is positioned to detect photoacoustic pressure wave signals 22 generated from structure 14. By way of example, data processor 30 may be an IBM AT compatible personal computer, although the scope of the invention includes the use of data processors other than that specifically identified above.

Robot positioner 28 may be a CIMROC 4000 Robot Controller manufactured by CIMCORP Precision Systems, Inc., Shoreview, Minn., although other commercially available industrial robots may also be employed in the implementation of the present invention. Techniques for controlling robotic positioner 28 so that it travels a predetermined path are well known by those of ordinary skill in the robotic field of technology.

Transducer 24 transforms photoacoustic pressure wave signals 22 into an analogous series of electrical pulses having pulse amplitudes corresponding to the intensity of the photoacoustic pressure wave signals 22. Transducer 24 may be realized using a PCP Piezotronics Model 106B50 piezoelectric sensor. Signal conditioner 26 receives the pulsed output signal of pressure transducer 24 and transforms it into a DC analog electrical output signal having a DC value proportional to the peak pulse amplitude of the signal received by signal conditioner 26. The output signal of signal conditioner 26 is received by data processor 30 as a variable control input signal. Based on the value of the control input signal, processor 30, using an appropriate processing routine, calculates (or otherwise determines) an appropriate robotic speed value between minimum and maximum values for the scan speed of robotic positioner 28, as described below. Data processor 30 then generates a speed control output signal to robot controller 29 that corresponds to the determined robotic scan speed value. Robotic controller 29 then directs robotic positioner 28 to travel at a speed corresponding to the speed control output signal.

In lieu of calculating a robotic speed value, for example, the output signal from signal conditioner 26 may be used as an address in a look-up table stored or generated by data processor 30 using appropriate processing software. Such software may retrieve a robotic speed value stored in particular address where the stored robotic speed value corresponds to a speed between minimum and maximum values. Data processor 30 then provides a scan speed control output signal based on that value to robot controller 28.

Figure 2:
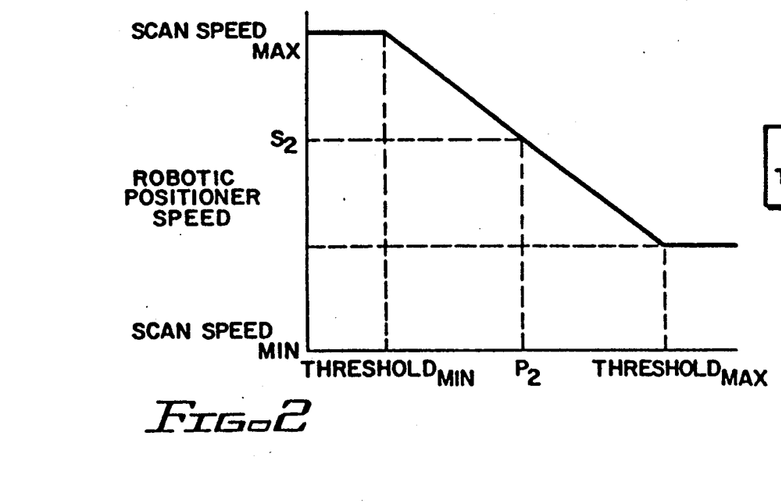
FIG. 2 is a graph illustrating the functional relation between the pulse amplitude of the signal produced by the acoustic transducer and the speed of the robotic positioner.

The speed value determined by processor 30 may be related to the peak pulse amplitude of the output signal of pressure transducer 24 by a decreasing function, as for example, linear with a negative slope, as shown in FIG. 2. Such function may be bounded within upper and lower speed limits. Examples of the relation between the speed value and the peak pulse amplitude are described below. In FIG. 2, if the peak pulse amplitude of the output signal 24a of pressure transducer 24 is equal to or less than a minimum average peak pulse threshold value, $Threshold_{min}$, then the speed value is determined to be a maximum scan speed value, Scan $Speed_{max}$. If the peak pulse amplitude of the output signal of pressure transducer 24 is equal to or greater than the maximum peak pulse threshold value, $Threshold_{max}$, then the speed value is determined to be the minimum scan speed, Scan $Speed_{min}$. If the peak pulse amplitude of the output signal 24a is equal to some amplitude $P_2$, then the speed value is determined to be $S_2$, where $Threshold_{Min} < P_2 < Threshold_{Max}$ and Scan-$Speed_{Max} > S_2$ ScanSpeed$_{Min}$. However, it is to be understood that there may be applications where it is desirable for the scan speed to be related to the output signal of pressure transducer 24 by an increasing function. Techniques for generating such an output signal from a digital data processor corresponding to a value determined by the processor are well known by those of ordinary skill in the art.

The values for $Threshold_{min}$ and $Threshold_{max}$ may be determined empirically as described below. A number of test scans are made using a light source such as light source 10 to irradiate a fresh sample structure representative of the structure that is to be processed by the method and system of the present invention. The operating parameters of the light source, such as modulation frequency and duty cycle may be varied for each test. Also, the distance between the light source and the test sample, referred to as the standoff distance, may be varied. A typical standoff distance is 1.0 inch. The photoacoustic pressure wave signals generated at the ablating surfaces of the test samples are detected by a pressure transducer such as pressure transducer 24 and recorded using suitable recording means. For example, photographs of an oscilloscope screen of an oscilloscope, or equivalent device, connected to receive and display the output signals from the pressure detector, may be taken. An individual (hereafter, "operator") then examines each of the test samples and determines, based on personal discretion, which ones have suitable finishes. Such discretion may consider the color and/or texture of the irradiated surface of the test sample. The operator then identifies the test sample having the most material removed, but still having an acceptable surface finish. The minimum threshold value, $Threshold_{min}$, is obtained by approximating the average value of the peak amplitudes of the photoacoustic pressure wave signals associated with that test sample. The operator may also identify the test sample having the least amount of material removed, but still having an acceptable surface finish. The maximum threshold value, $Threshold_{max}$, is obtained by approximating the average value of the amplitudes of the photoacoustic pressure wave signals associated with this latter test sample.

Another way to determine the minimum and maximum threshold values is to perform the steps described in the preceding paragraph, but to also scan the test sample at different speeds while the test sample is being irradiated. Then, the test sample having the least amount of material removed, but still having an acceptable finish is identified. The maximum threshold value is obtained from the amplitude of the photoacoustic pressure wave signals generated from the surface of that test sample in accordance with the methods described in the preceding paragraph. The scan rate at which this test sample was run then becomes the minimum scan speed, Scan $Speed_{min}$. The test sample having the most material removed, but still having an acceptable surface finish is identified. The minimum threshold value is obtained from the amplitude of the photoacoustic pressure wave signals generated from the surface of that test sample. The rate at which this test sample was run becomes the maximum scan speed, Scan $Speed_{max}$. Determination of the minimum and maximum scan speeds are described in greater detail below.

The maximum scan speed is determined, for example, by first observing the maximum scan rate at which beam 12 irradiates a "footprint" of the surface and still remove sufficient material. The footprint is that area ablated by light source 10 while the scan speed of the light beam is zero. The maximum scan rate may then be established at a rate somewhat less than the maximum observed scan rate in order to provide for a margin of error. A high scan rate is desirable because it reduces the time required to expose the desired material. However, if the scan rate is too high, insufficient material will be removed to fully expose the desired material. It is preferable to provide the maximum scan rate with a safety factor to account for experimental error and variations in the characteristics of the structure having the surface to be exposed. A maximum scan rate may be established which is slightly less than the maximum acceptable observed scan rate that resulted in exposure of the selected surface having an acceptable surface finish. For example, if the maximum observed acceptable scan rate is 2.0 inches/second and a safety factor of 10 percent is desired, the maximum scan rate may be established at 1.8 inches/second.

The minimum scan rate of robotic positioner 28 is established by first observing the slowest speed at which light beam 12 can scan the surface without damaging the surface to be exposed. Damage occurs if the area being irradiated is exposed to too much light energy, which when absorbed, is transformed into heat. As with the maximum scan rate, it is preferable to incorporate example, assuming the slowest acceptable observed scan rate is 2.0 inches/second and a safety factor of 10 percent is desired, the minimum scan rate may be established at 1.8 inches/second.

Data processor 30 may be suitably programmed so as to determine a scan speed, between minimum and maximum scan speeds, which is functionally related to a digital representation of the peak intensities transducer 24. Such function may be increasing or decreasing, depending upon the particular application.

Again referring to FIG. 1, nozzle 34, mounted to robotic positioner 28, ejects a particle stream, as for example, carbon dioxide pellets 32 which are directed to impinge, and thereby cool, structure 14 at an area that has just been heated as a result of being irradiated by light beam 12. Pellets are supplied to nozzle 34 from a carbon dioxide pellet source 36 which may be of the type commercially available from Cold Jet, Inc., Loveland, Ohio. Pellets 32 also sweep away ablated materials and prevent their condensation on emitting window 13 or structure 14. The ablated materials and expended particle stream materials 80a are sucked away from the area being ablated through nozzle 80 and duct 82, and are collected by vacuum system 84. However, it is to be understood that the particle stream may also be comprised of dry gas, liquid, or other solid particles entrained in a gas.

Figure 3A:
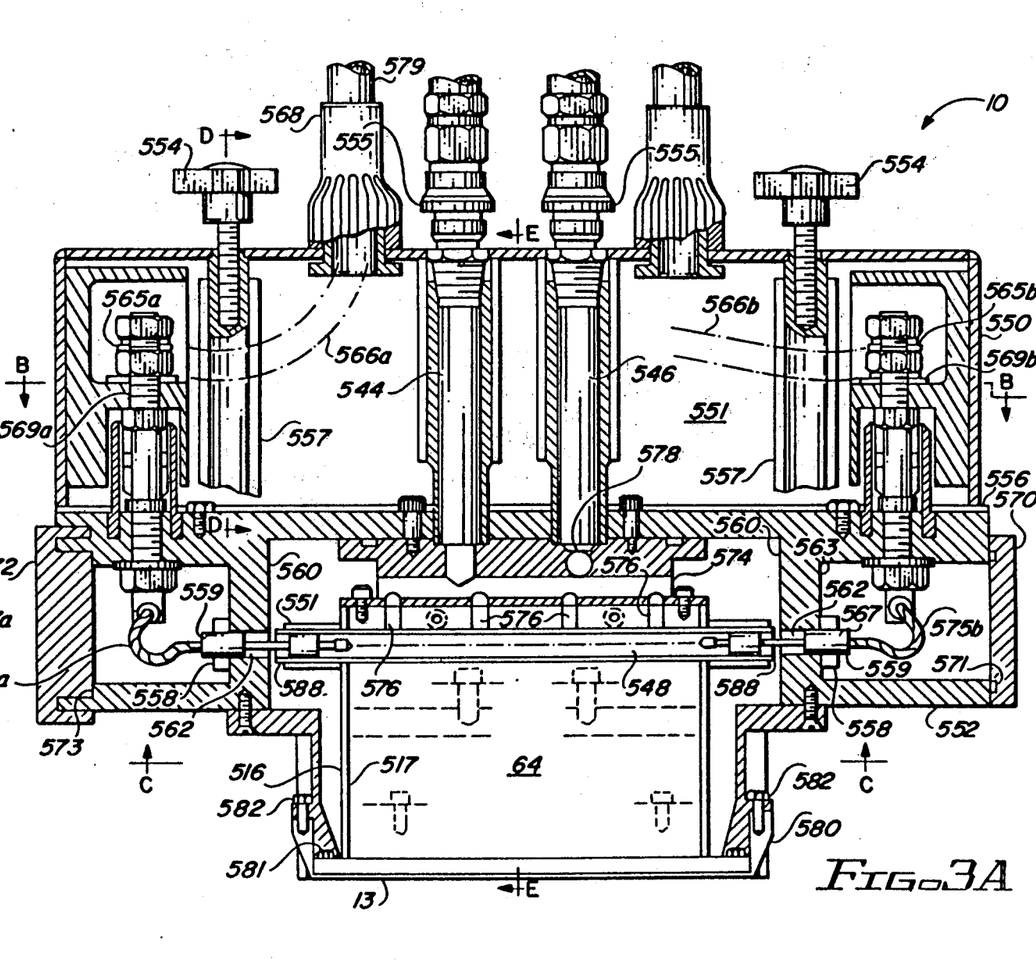
FIG. 3A is a front, cross-sectional, elevation view of a flashlamp mounted in a housing.
Figure 3B:
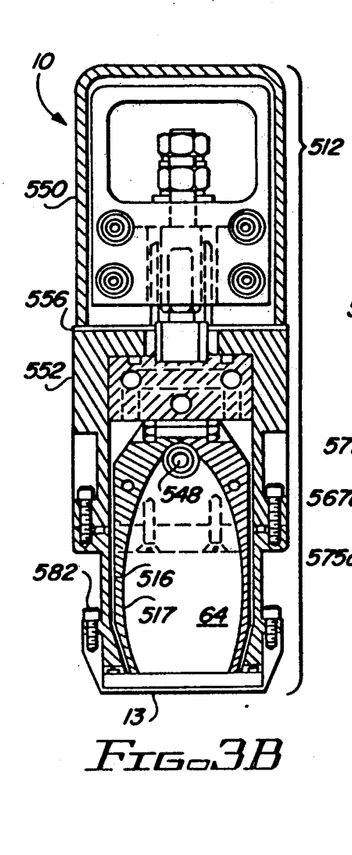
FIG. 3B is a side, cross-sectional, elevation view of the flashlamp mounted in the housing.

Referring to FIGS. 3A and 3B, light source 10 preferably includes broadband xenon flashlamp 548 mounted in housing 512. Broadband optical energy generally refers to optical energy that includes spectral components with wavelengths that may range from 170 nm to 5000 nm. A flashlamp or flashtube is a gas filled device which converts electrical energy to optical energy by passing current through a plasma typically contained in a transparent tube through which the optical energy is transmitted. Housing 512 includes upper housing 550 attached to lower housing 552 by fasteners 554. Reflector 516 is mounted in lower housing 570 so that portions of light generated by flashlamp 548 are reflected out of housing 512 through quartz window 13. Housing 512 may be fabricated from black, hard anodized aluminum. Gasket 556 is interposed between upper and lower housings 550 and 552 to keep moist air from penetrating chamber 551 in upper housing 550. Electrical connectors 567 at the ends of optical energy source 514 are supported in and extend through apertures 562 in walls 563 of lower housing 552. Flashlamp 548 is positioned within fused quartz water jacket 551 mounted between walls 563 of lower housing 552. The position of flashlamp 548 is maintained by "O"-ring compression fittings 558 that fit over electrical connectors 567a and 567b, and are fastened to walls 563 by threaded fasteners, not shown. "O"-rings 559 interposed between compression fittings 558 and walls 563 provided a water tight seal therebetween. By way of example, reflector 516 may have an elliptical cross-section as shown in FIG. 3B, having a major axis of 7.00 cm, a minor axis of 2.80 cm, and a length of about 15.00 cm. In such case, the longitudinal axis of flashlamp 548 is generally coincident with a focus of reflector 516. However, it is to be understood that the cross-section of reflector 516 may be shaped in a variety of ways, preferably for example, as a keyhole or cusp.

Referring to FIG. 3A, access to flashlamp 548 is obtained through removable access plates 570 and 572 releasably mounted to lower housing 552 by means, not shown, as would be known by those skilled in the art. "O"-ring 571 provides a watertight seal between access plate 570 and lower housing 552. Likewise, "O"-ring 573 provides a watertight seal between access plate 572 and lower housing 552.

Electrical power to energize flashlamp 548 is conventionally provided by high voltage coaxial cable 579 that penetrates upper housing 550 through cable fitting 568 and includes center conductor 566a and braided conductor strap 566b. Center conductor 566 is conventionally connected to high voltage terminal post 569a with a lug 565 soldered or brazed to the center conductor. Terminal post 569a is electrically connected to flashlamp 548 via braided cable 575a brazed to high voltage electrical connector 567a. Electrical return is provided by braided cable 575b brazed or soldered to low voltage electrical connector 576b and to terminal post 569b. The end of braided conductor strap 566b is terminated with lug 565b which is connected to terminal post 569b.

Flashlamp 548 may be removed from lower housing 552 as follows: First, electrical power must be disconnected from housing 512. Then, quick connect fittings 555 are disconnected from inlet and outlet tubes 544 and 546, respectively. Fasteners 554 are removed from stations 557 connected to lower housing 552 so that the lower housing may be separated from upper housing 550. Then, access plates 570 and 572 are removed from lower housing 552. Braided cables 575a and 575b are unbolted from terminal posts 569a and 569b, respectively. Compression fittings 558 are unfastened from walls 563 and slipped out over their respective braided cables 575a and 575b. Then, flashlamp 548 may be carefully slipped out of water jacket 547 through either of apertures 562 and out of lower housing 552. Replacement of flashlamp 548 is accomplished by performing in reverse order, the steps recited above for removing the flashlamp.

Light generated by flashlamp 548 is emitted through quartz water jacket 551 and exits lower housing 552 through window 13 either directly, or by reflecting off of reflective surface 517 of reflector 516. Window 13 is preferably manufactured of fused quartz because such material has excellent transparency and high resistance to heat. Further, the transparency of quartz does not degrade from exposure to ultraviolet light. Gasket 581 is interposed between window 13 and window frame 580 so that the window is held in a watertight arrangement to lower housing 552 by bolts 582.

Flashlamp 548 and reflector 516 are preferably cooled with deionized water having a temperature, for example, of about 50° F. supplied at a rate of about 2 gpm from a water supply (not shown) to housing 512 through inlet tube 544 and returned through outlet tube 546. The deionized water preferably has an electrical resistance of at least 1 megohm. Inlet tube 544 penetrates upper housing 512 and is connected to manifold 574, mounted in lower housing 552, having multiple outlets 576 which penetrate reflector cavity 564 to distribute water over the length of flashlamp 548 and fill the reflector cavity. Water also penetrates the tapered ends 588 of quartz water jacket 551 to cool electrical connectors 567a and 567b, and flashlamp 548. Heat resulting from the generation of radiant energy from flashlamp 548 is absorbed by the water and transported out of chamber 564 through port 578 in fluid communication with outlet tube 546.

It is well known that in order to maximize the service life of a flashlamp, the operation of the flashlamp should be critically damped, that is, it should be operated with a dampening coefficient of about 0.77. Factors that determine the dampening coefficient of a flashlamp include: inductance of a single mesh pulse forming network ("PFN") typically employed in a flashlamp power circuit, capacitance, C, of the PFN, arc length of the flashlamp, and operating voltage, V, across the terminals of the flashlamp. The energy output, E, of a flashlamp is characterized by the relation $E=CV^2$. However, V should only be varied by no more than about ± 5 percent of the optimum voltage in order to maximize service life. Further, it is not practical to vary C because of the expense of additional capacitors required to implement such a circuit and because of the life limiting character of this type of circuit. Therefore, in order to maximize the useful life of flashlamp 548, it is preferably operated at a constant repetition rate with a fixed pulse width.

By way of example only, flashlamp 548 may be configured as having a tube filled with xenon gas at a pressure of 60.0 KPa, an overall length of 28 cm, a 7 mm inside diameter, 9 mm outside diameter, and 15 cm arc length. This particular flashlamp is preferably operated at a repetition rate of 4-5 Hz with a full-width, half-maximum ("FWHM") fixed pulse width in the range of 1200-1800 microseconds and an input energy of about 100-120 joules/cm of arc length. As is characteristic, the useful output energy of a flashlamp available to irradiate the surface of structure 14 is approximately 20-25 percent of the input energy to the flashlamp. The flashlamp is powered by a suitable power supply, not shown, as would be known by those of ordinary skill in the art.

Because flashlamp 548 is operated with a damping coefficient of about 0.77, the preferred method of controlling the energy flux (joules/second) at the surface of structure 14 is to establish an appropriate distance between the flashlamp and the surface of the structure since the incident energy intensity at the surface of the structure is generally inversely proportional to the distance between the surface and the flashlamp. The distance between the flashlamp and the surface of structure 14 is more conveniently discussed with reference to the standoff distance, d, between the surface of the structure and window 13, since the window and the flashlamp are a fixed distance apart.

Although the preferred embodiment utilizes a broadband flashlamp to generate light beam 12, the invention may also employ other types of pulsed light sources that generate visible or ultraviolet light. Such light source may also include a laser. The output of a broadband flashlamp offers the advantage of providing electromagnetic spectrum components which may have high probabilities of being absorbed by the different types of materials to be subjected to the method and process of the present invention.

Light control circuit 11 may be of the type described in U.S. patent application Ser. No. 07/645,372, entitled "Ruggedized Flashlamp Exhibiting High Average Power and Long Life," by Richard G. Morton and William J. Connally, filed Jan. 24, 1991, assigned to the same assignee as the present application, and incorporated herein by reference.

Figure 4A:
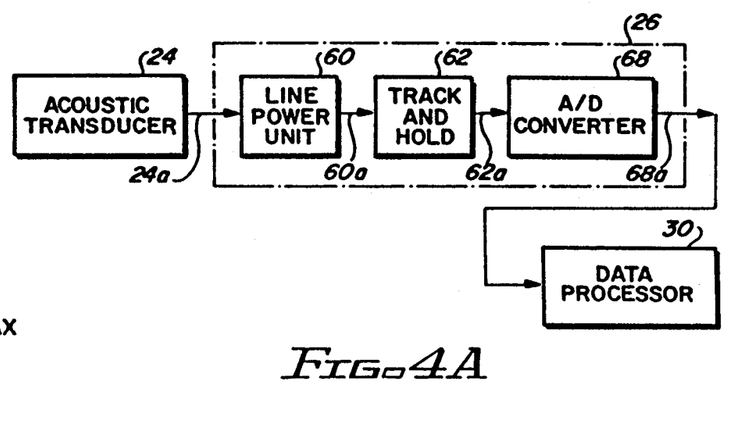
FIG. 4A is a block diagram showing the signal conditioning circuit in greater detail than presented in FIG. 1.
Figure 4B:
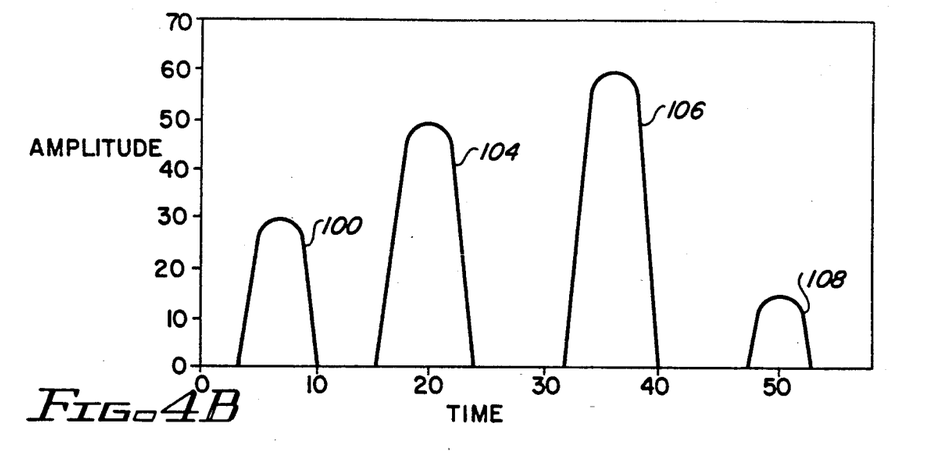
FIG. 4B shows a graph of the output of line power unit 60 as a function of time.
Figure 4C:
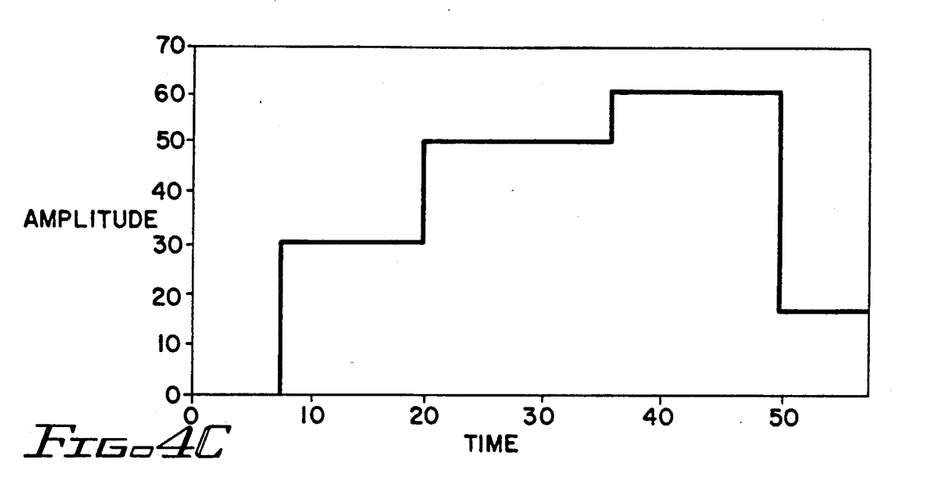
FIG. 4C shows a graph of the output of track-and-hold circuit 62 as a function of time.

FIG. 4A shows a more detailed view of the signal conditioning circuit 26. As seen in FIG. 4A, such conditioning circuit 26 is comprised of several elements. A line power unit 60 maintains the pulse train signal received via signal line 24a from pressure transducer 24 ground-based and at positive polarity. (Hereinafter, it is noted that the signal appearing or present on a given signal line may be referred to using the same reference number as the signal line. That is, e.g., the pulse train signal provided by acoustic transducer 24 on signal line 24a may also be referred to as "signal 24a".) Line power unit 60 thus provides a positive signal 60a to sample-and-hold unit 62. Track-and-hold unit 62 holds the peak value of output signal 60a until the next pulse arrives and provides an output signal 62a representing the peak amplitude of each pulse of output signal 60a, as illustrated in FIGS. 4B and 4C. By way of example, FIG. 4B presents a typical output signal 60a of line power unit 60 consisting of pulse 100 having a peak amplitude of 30 at time t=7, pulse 104 having a peak amplitude of 50 at t=20, pulse 106 having a peak amplitude of 60 at t=36, and pulse 108 having a peak amplitude of 15 at t=50, where t represents time and the units of amplitude and time are arbitrary. (For example, the amplitude units may be millivolts, and the time units may be milliseconds). The output signal 62a of track-and-hold circuit 62 is directed to A/D converter 68 in response to receiving a reset signal from processor 30. In accordance with the example above described with reference to FIG. 4B, and now also referring to FIG. 4C, signal 62a has amplitude 30 over the time interval 7-20, amplitude 50 over the time interval 20-36, amplitude 60 over the time interval 36-50, and amplitude 15 from the time interval beginning at t=50.

The output signal 62a of track-and-hold circuit 62 is scaled and converted into a digital output signal 68a by A/D converter 68. Digital output signal 68a is provided as the variable input to data processor 30, as discussed above. Data processor 30, in turn, outputs a speed control signal to robotic controller 29 in order to drive robotic positioner 28 at the appropriate speed along a predetermined path. Data processor 30 also generates a clocked reset signal 30a which triggers track-and-hold circuit 62 to provide signal 62a to A/D converter 68.

Figure 5:
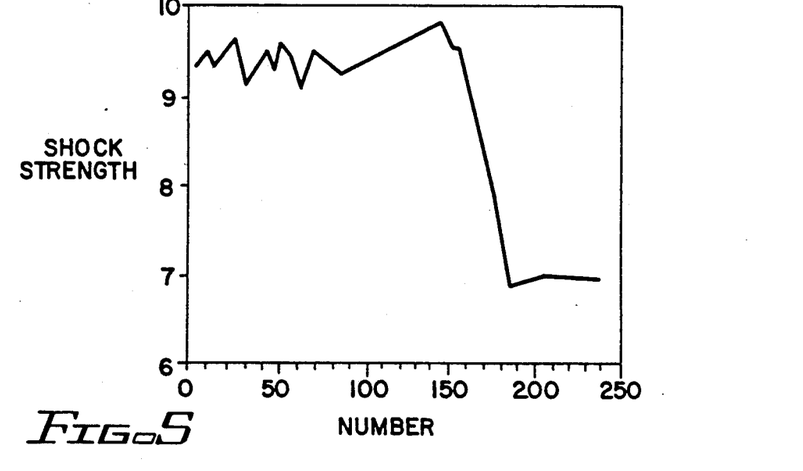
FIG. 5 illustrates the photoacoustic signature of yellow primer being ablated from an aluminum substrate by a KrF excimer laser.

FIG. 5 illustrates the photoacoustic pressure wave signal of yellow primer when ablated from an aluminum substrate. using a series of radiant energy pulses. The amplitude of the photoacoustic signature corresponding to pulse numbers 0-150 had a shock strength that averaged about 9.3 lbs/in$^2$ which corresponds to the photoacoustic pressure waves of yellow primer (MIL-P-23377) being ablated by an excimer laser. The output of the laser was modulated at a frequency of 10 Hz and had a duty of cycle of $2\times10^{-7}$. The photoacoustic pressure waves were detected with a PCP Piezotronics Model 106B50 piezoelectric sensor and provided to an oscilloscope. Each pulse number represents a laser pulse impinging the primer with an intensity of 3.8 joules/cm$^2$. As seen in FIG. 5, the shock strength of the primer rapidly diminished between pulse numbers 150 and 180, indicating that a decreasing amount of material was being ablated. From about pulse number 180 and higher, it can be seen that the pulse amplitudes had a strength of approximately 7 mv, indicating that the laser was irradiating a different material than the one previously ablated, which in this example was aluminum. The difference in the photoacoustic pressure wave signals between the primer and the aluminum is thus clearly distinguishable.

Figure 6:
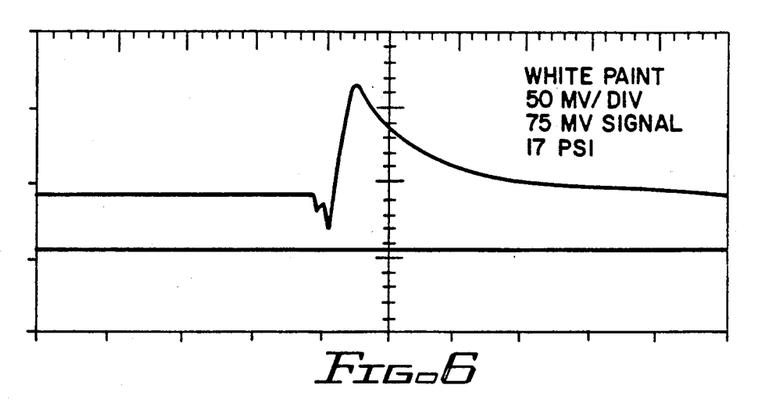
FIG. 6 illustrates the photoacoustic pressure wave signal resulting from white paint being ablated from an aluminum surface.
Figure 7:
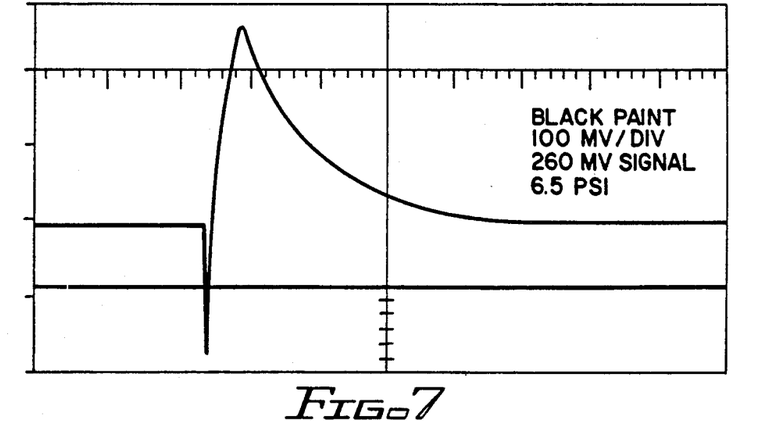
FIG. 7 illustrates the photoacoustic pressure wave signal resulting from black paint being ablated from an aluminum surface.

FIG. 6 illustrates the electrical analog of the photoacoustic pressure wave signals resulting from the ablation of white paint on an aluminum surface irradiated with a single pulse of a Xenon flashlamp at an intensity of 15 J/cm$^2$. The photoacoustic pressure wave signals were detected using a PCP Piezotronics Model 106B50 piezoelectric sensor having an output directed to an oscilloscope. In FIG. 6, the pulse amplitude is represented on the vertical axis by 50 mv/division, and time is represented on the horizontal axis by 1 seconds/division. FIG. 7 similarly illustrates the electrical analog of the photoacoustic pressure wave signals resulting from the ablation of black paint from an aluminum surface, where the vertical axis is scaled at 100 mv/division and the horizontal axis is scaled at 1 millisecond /division. The photoacoustic pressure wave signals of the black paint were obtained in the same manner as the photoacoustic pressure wave signals of the white paint. Accounting for the difference in the scales along the ordinate axes between FIGS. 6 and 7, the maximum pulse amplitude for the white paint is about 130 mv and the maximum pulse amplitude for the black paint is about 650 mv.

Hence, it can be seen that the differences in the photoacoustic pressure wave signals between black and white paint is readily distinguishable by the electrical circuitry described with reference to FIG. 4A.

Thus, the present invention may be employed to remove layers of coatings of a structure to expose a selected substrate in an automated process controlled by the photoacoustic signature pressure pulses generated by the irradiated layers. For this embodiment, it is preferable that the structure be sufficiently irradiated to ablate all of the materials that are to be removed, but not to an extent which damages the layer to be exposed.

Figure 8:
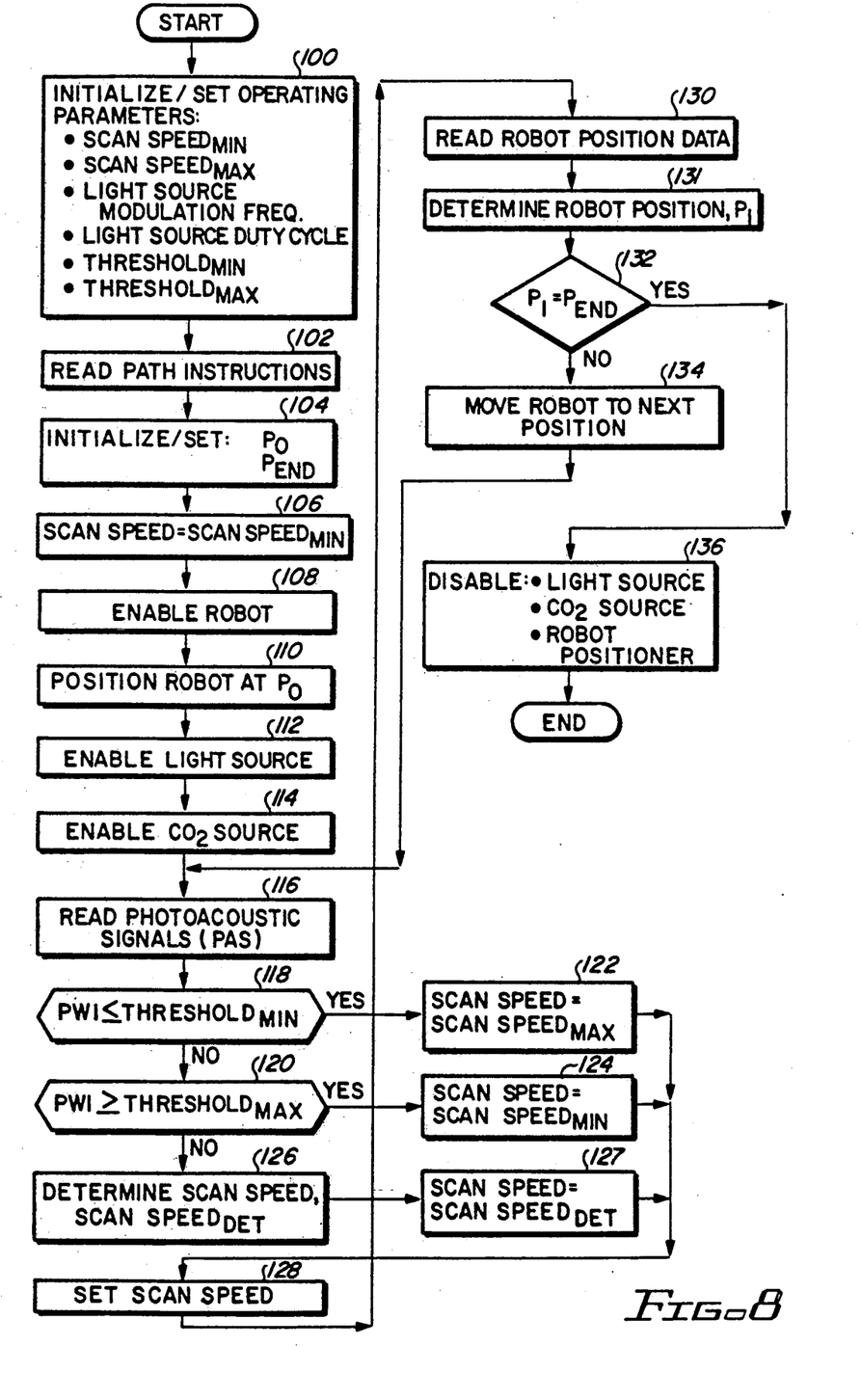
FIG. 8 is a flowchart representing the process of an example of one embodiment of the present invention.

The operation of the method and system of the above described embodiment of the present invention may be more fully appreciated with reference to the flowchart presented in FIG. 8 and the following discussion. The operating parameters for the minimum and maximum scan speeds of robotic positioner 28 (Scan Speed$_{min}$ and Scan Speed$_{max}$, respectively), as well as the modulation frequency and duty cycle for light source 10 are initialized at step 100. Path instructions are input into and read by data processor 30 at step 102. The path instructions define the predetermined path of robotic positioner 28. Then, based on the path instructions, values corresponding to the initial position, $P_o$, and the end position, $P_{end}$, of robotic positioner 28 are set at step 104. Next, the initial scan speed of robotic positioner 28 is set equal to the minimum scan speed, Scan Speed$_{min}$ at step 106. Robotic positioner 28 is enabled at step 108 and moved to its initial position, $P_o$ at step 110. At steps 112 and 114, light source 10 and carbon dioxide pellet source 36 are enabled. At this stage, light source 10 is irradiating structure 14 at an appropriate location and the system is ready to analyze data used to control the process.

Pressure transducer 24 detects photoacoustic pressure wave signals generated by the ablated materials of structure 14 which are processed by signal conditioning circuit 26 and provided to data processor 30 for analysis at step 116. At step 118, data processor 30 determines if the intensity of the photoacoustic pressure wave signals ("PWI") are equal to or less than a minimum threshold value, Threshold$_{min}$. If that determination is YES, then the process proceeds to step 122 where data processor 30 defines the value for the scan speed, Scan Speed, to be equal to the maximum scan speed, Scan Speed$_{max}$. If the determination at step 118 is NO, then data processor 30 determines if the intensity of the photoacoustic pressure wave signal is equal to or greater than the maximum threshold value, Threshold$_{max}$. If the determination at step 120 is YES, data processor 30 defines the scan speed to be equal to the minimum scan speed, Scan Speed$_{min}$. If the determination at step 120 is NO, then data processor 30 determines the scan speed, as previously described herein, at step 126 and sets the variable corresponding to the scan speed equal to the determined scan speed at step 127.

Next, data processor 30 provides a scan speed control output signal to robotic controller 29 at step 128 which directs robotic positioner 28 to move at the appropriate scan speed.

Next, data processor 30 reads data representative of the position of robotic positioner 28 at step 130 and determines the position of robotic positioner 28 at step 131. One method by which the position of robotic may be determined uses a feedback signal 29a provided from robotic controller 29 to data processor 30. Feedback signal 29a may include the output signals of one or more rotary shaft encoders, not shown, having phase-quadrature output signals. Feedback signal 29a typically includes data from one rotary shaft encoder for each axis of motion necessary to define the position of robotic positioner 28, as for example, by coordinates of the X, Y, and Z axes, as well as any rotational axes. Techniques for providing data necessary to define the position of a robot actuator and for interpreting such data are well known by those of ordinary skill in the art.

After the position of robotic positioner 28 has been determined, a decision is made at step 132 as to whether the position, $P_1$, of robotic positioner 28 is the position at the end of the predetermined path, $P_{end}$, defined by the path instructions at step 102. If the determination at step 132 is YES, then the processing of structure 14 is complete, since light source 10 has scanned the entire predetermined path. Then, at step 136, data processor 30 provides output signals to disable carbon dioxide pellet source 36, robotic controller 29 disable robotic positioner 28, and light control circuit 11 to disable light source 10. However, if the determination at step 132 is NO, then light source 10 has not scanned the entire predetermined path along structure 14, indicating structure 14 has not been completely processed. Then, the process continues at step 116, described above.

A major feature of this invention is that the process is controlled by varying the scan speed as a function of the peak pulse amplitude of the photoacoustic pressure wave signals. This control technique promotes a long and useful service life of the light source as opposed to systems in which the photoacoustic pressure wave signals are used to control modulation of the output of the PAS generating light source.

In the example of the preferred embodiment described above, the amplitude of the pressure wave signal pulses is used as an input to control the speed of a robotic positioner. By way of example, it has been found that when removing painted coatings such as polyurethanes from aluminum substrates, such as aircraft surfaces, the speed at which light source 10 scans structure 14 ranges from about 0.5 in./sec. for 6-8 mil highly reflective paint (nominal) to about 1.0 in./sec for 6-8 mil, highly absorptive paint.

In one experiment, a broadband xenon flashlamp was used to expose an aluminum surface of a structure comprising an aluminum substrate (2024-T3, bare) having a thickness of 0.032 inches coated with a 0.001-0.002 inch layer of epoxy primer (MIL-P-23377) and a 0.006 inch polyurethane topcoat (MIL-C-83286) formed on the primer. The flashlamp was modulated to have an output of 4 Hz with a 1500 microsecond pulse width. The standoff distance between the light source and the structure was 0.38 inches, whereby the structure was irradiated at a nominal intensity of 9–10 joules/cm$^2$ with an effective footprint about 0.125 inches wide. The light source scanned the structure at a nominal speed of 0.06 inches/second, providing a surface exposure rate of 0.36 in$^2$/second. Using these values, both the topcoat and primer were removed from the structure. However, it is to be understood that in the implementation of the present invention, structures, such as structure 14, may be irradiated with an incident intensity that may range from 1–30 joules/cm$^2$, where incident intensity refers to the intensity of the optical energy at the surface of the structure. The appropriate incident intensity depends on such factors as the thermal and reflective characteristics of the particular material being processed.

It is to be understood that the parameters and data presented in the preceding paragraph are provided by way of example only, and are not to be construed as limiting the scope of the invention. For example, the pulse widths of the output of the light source and the scan rate may be determined empirically in accordance with the requirements of a particular application. For example, pulse widths of 2400 microseconds are well suited for exposing the surfaces of metal substrates, whereas pulse widths of 1200 microseconds are more appropriate for exposing the surfaces of epoxy composites which are less tolerant of heat. Furthermore, the scan speed of the light source may be varied depending on factors such as the type and thickness of the materials to be removed.

While the present invention has been described with reference to removal of paint from a metal substrate, the invention may be more generally employed. For example, the invention could be used to remove oxidation from a metal substrate, such as ferrous oxide (rust) from steel. The invention may also be employed to remove coatings from non-metallic substrates.

In a second embodiment of the present invention, the photoacoustic signature signals from different coatings may be used as a basis to control a system for exposing a predetermined layer of a multilayered structure. The embodiment takes advantage of the fact that materials may be identified by their photoacoustic pressure wave peak intensities. Referring to FIG. 1, the second embodiment differs from the first embodiment in the way data processor 30 utilizes information corresponding to the photoacoustic pressure wave signals received from signal conditioning circuit 26.

Figure 1:
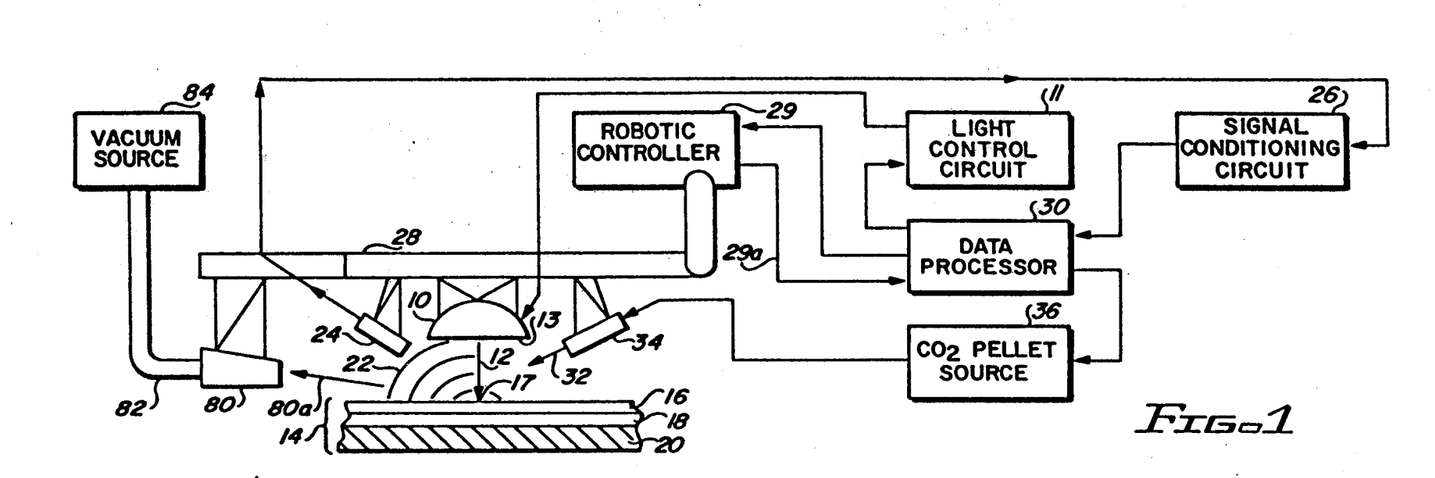
FIG. 1 is a block diagram of an example of an embodiment of the present invention which selectively removes one or more material layers from a structure so as to expose a desired surface.

Referring to FIG. 1, the second embodiment is described with reference to structure 14, where for purposes of illustration, structure 14 may have an aluminum substrate 20, a middle layer 18 of black paint, and an outer layer 16 of white paint, and it is desired to remove the white paint to expose the black paint. First, a small discrete area of layer 16 is removed to expose the desired material at layer 18. Then, the human operator manually controls light source 10 to irradiate a sample area of layer 18 in order to generate photoacoustic pressure wave signals characteristic of that layer as it ablates. The peak amplitude of these reference signals are used to establish a reference value which is stored in data processor 30 and which will be compared to the amplitudes of photoacoustic signals generated by ablation of structure 14. From FIGS. 6 and 7, it can be seen that the maximum pulse amplitude for the white paint is represented by about 130 mv and the maximum pulse amplitude for the black paint is about 650 mv. So a reference value is selected to represent ablation of the black layer, i.e., at $650 \pm \delta$, where $\delta$ represents a tolerance limit.

Next, structure 14 is irradiated by light source 10 while the light source scans the structure at a maximum scan speed to prevent damaging the layer to be exposed, i.e., layer 18 of black paint. Such maximum scan speed may be determined as previously discussed herein. While the surface of the structure is being ablated, processor 30 continuously compares the amplitude of the photoacoustic pressure wave ("PAS") generated by the ablating materials. Initially, the PAS signals generated by the white paint (layer 16) have an amplitude of about 130 mv. The difference between the reference value and the amplitude of the white paint pressure wave signals $[(650 \pm \delta) - 130]$ indicates that layer 16 has not been fully removed. At first, the difference between the PAS signals from the white paint and the reference value is relatively high. Therefore, the scan speed of the robotic positioner is modified to be relatively slow, as for example, a minimum scan speed, to assure removal of the white paint. However, as the amount of white paint remaining in the irradiated area diminishes, the black paint becomes exposed, and generates its own PAS signals having amplitudes of about 650 mv. The difference between the amplitude of the detected PAS signals and the reference value becomes prgressively less as more black paint is exposed. Therefore, the difference between the reference value and the PAS signals generated at the surface of the structure diminishes. Continued exposure of black paint results in a progressive increase in the scan speed of the robotic positioner to prevent damaging the black paint. Then, when the difference between the reference value and the PAS signals is less than some threshold value, the scan speed is controlled to be a maximum scan speed to prevent ablating too much black paint. The scan speed is maintained at the maximum speed until the difference between the PAS signals and the reference become greater than a minimum threshold value.

Figure 9:
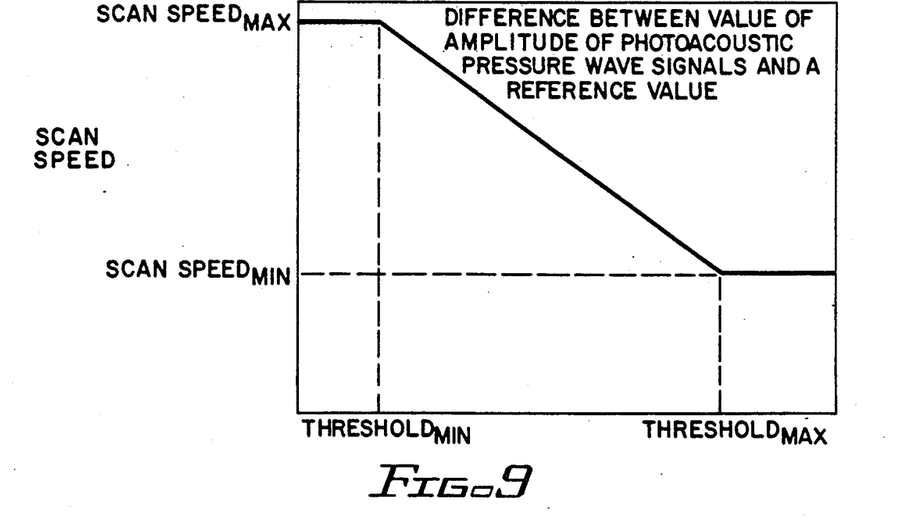
FIG. 9 shows a graph illustrating the functional relation between the scan speed and the difference between the photoacoustic pressure wave signals and a reference signal.

Data processor 30 outputs speed control signals functionally related to the difference between the amplitude of the detected PAS signals and the reference value. For example, if the difference between the value of the amplitude of photoacoustic pressure wave ("PAS") signals and the reference value is equal to or less than some minimum threshold value, then the scan speed of the robotic positioner may be controlled to be a maximum scan speed. If the difference between the value of the amplitude of the PAS signals and the reference value is equal to or greater than a maximum threshold value, the scan speed may be controlled to be a minimum scan speed. However, if the value of the amplitude of the PAS signals is greater than the minimum threshold value, but less than the maximum threshold value, then the scan speed is controlled such that the value of the scan speed is functionally related to such difference by a decreasing function, which may for example, be linear, as shown in FIG. 9.

This embodiment operates most effectively where, as in the example above, the photoacoustic pressure wave signals generated by the different materials in layers 16 and 18 are distinguishable. Although the second embodiment has been described with reference to a specific example, it is to be understood that the scope of the invention can be generalized to expose a selected layer of material of a structure having any number of layers comprised of material combinations other than those identified above.

While the present invention has been described in terms of preferred embodiments, it is to be understood that the invention is not to be limited to the exact form of the apparatus or processes disclosed. Therefore, it is to be understood that the invention may be practiced other than as specifically described without departing from the scope of the claims.

What is claimed is:

1. A system for removing material from a substrate, comprising:
   a light source for directing a light beam to irradiate a structure comprising at least one layer of material formed on a substrate at an intensity sufficient to ablate said material so that said ablating material generates photoacoustic pressure wave signals having peak intensities;
   a fast pressure transducer positioned to detect said photoacoustic pressure wave signals and provide a first output signal corresponding to said photoacoustic pressure wave signals having peak intensities;
   control means coupled to receive said first output from said fast pressure transducer for providing a speed control signal where said speed control signal is functionally related to said photoacoustic pressure wave signal peak intensities; and
   means coupled to receive said speed control signal for conveying said light source and said fast pressure transducer along a predetermined path so that said light source irradiates said structure at a scan speed controlled by said speed control signal.

2. The system of claim 1 wherein:
   said control means directs said scan speed to be a minimum scan speed if said photoacoustic pressure wave signal peak intensities are equal to or greater than a first threshold value; and
   said control means directs said scan speed to be a maximum scan speed if said photoacoustic pressure wave signals peak intensities are equal to or less than a second threshold value.

3. The system of claim 2 wherein said control means includes:
   signal conditioning circuit means coupled to receive said first output signal from said fast pressure transducer for generating a second output signal corresponding to said photoacoustic pressure wave signals peak intensities; and
   a data processor coupled to receive said second output signal from said signal conditioning circuit for generating and providing said speed control signal to said conveying means.

4. The system of claim 3 wherein said structure is irradiated by said light beam at an incident intensity ranging from about 1-30 joules/cm$^2$.

5. The system of claim 4 wherein said light beam is modulated at a frequency of 4-5 Hz.

6. The system of claim 5 wherein said second output signal of said signal conditioning circuit is a DC output signal corresponding to said peak intensities of said photoacoustic pressure wave signals.

7. The system of claim 6 which further includes means for cooling said structure to prevent said light beam from causing heat damage to said structure and for cleaning said structure.

8. The system of claim 7 wherein said cooling means directs a stream of particles to impinge said structure.

9. The system of claim 8 wherein said stream of particles includes carbon dioxide pellets entrained in a dry flowing gas stream.

10. The system of claim 6 wherein said light source includes a broadband flashlamp for generating said light beam.

11. The system of claim 10 wherein said conveying means is a robotic positioner system 12. The system of claim 11 wherein said light source further includes:
    a water cooled housing having a quartz window; and
    a reflector having an elliptical reflective surface with an elliptically shaped cross-section and a focus mounted in said housing so that light generated at said focus reflects off said reflective surface and is transmitted through said quartz window; whereby said flashlamp is mounted substantially coincident along said focus.

13. The system of claim 11 wherein said signal conditioning circuit includes:
    a track-and-hold circuit for receiving said first output signal from said fast pressure transducer; and providing an output corresponding to said peak intensity of said photoacoustic pressure wave signals in response to receiving a reset signal generated by said data processor; and
    an analog-to-digital converter operably coupled to said output from said track-and-hold for providing a digital output to said data processor.

14. A method for removing material, comprising the steps of:
    (1) irradiating a structure comprising at least one layer of material formed on a substrate with a light beam having an intensity sufficient to ablate said materials in order to expose selected regions of said substrate, where said ablated material generates photoacoustic pressure wave signals having peak intensities;
    (2) scanning said structure with said light beam;
    (3) detecting said photoacoustic pressure wave signals;
    (4) determining an updated scan speed functionally related to said peak intensities of said detected photoacoustic pressure wave signals; and
    (5) directing said scan speed to be equal to said updated scan speed.

15. The method of claim 14 including irradiating said structure at an incident intensity ranging from about 1-30 joules/cm$^2$.

16. The method of claim 15 wherein said scan speed is related to said intensities of said photoacoustic pressure wave signals by a monotonic decreasing function.

17. The method of claim 16 including:
    (1) directing said scan speed to be a minimum speed if said peak intensities of said photoacoustic pressure wave signals are equal to or greater than a first threshold value; and
    (2) directing said scan speed to be a maximum scan speed if said peak intensities of said photoacoustic pressure wave signals are equal to or less than a second threshold value.

18. The method of claim 17 including generating said light beam with a broadband flashlamp.

19. The method system of claim 18 including modulating said light beam at a frequency of 4-5 Hz.

20. The method of claim 19 including cooling said structure to prevent said light beam from causing heat damage to said structure.

21. The method of claim 20 including cooling and cleaning said structure by impinging a particle stream on said structure.

22. The method of claim 20 including impinging a particle stream including carbon dioxide pellets entrained in a dry gas on said structure.

23. A method for exposing a selected layer of a multi-layered structure, comprising the steps of:
   1) irradiating the surface of a structure formed of one or more layers of material formed on a substrate at a first location with a light beam having sufficient intensity to ablate said irradiated material, where said material generates photoacoustic pressure wave signals having peak intensities in response to being irradiated;
   2) detecting said photoacoustic pressure wave signals generated by said irradiated surface;
   3) comparing representations of said peak intensities of said photoacoustic pressure wave signals with a reference value corresponding to a photoacoustic pressure wave signal of a material comprising said selected layer to be exposed; and
   4) directing said light source to irradiate said surface at a scan speed functionally related to a difference between said representations of said peak intensities of said photoacoustic pressure wave signals and said reference value.

24. The method of claim 23 including generating said light beam with a broadband flashlamp.

25. The method system of claim 24 including modulating said light beam at a frequency of 4-5 Hz.

26. The method of claim 23 including cooling said structure to prevent said light beam from causing heat damage to said structure by impinging a particle stream on said structure.

27. The method of claim 26 including cooling and cleaning said structure by impinging a particle stream comprised of carbon dioxide pellets entrained in a dry flowing gas stream on said structure.

28. A system for exposing a selected layer of a multi-layered structure, comprising:
   a radient energy source for irradiating the surface material of a structure comprising one or more layers of material formed on a substrate with radient energy having sufficient intensity to ablate said irradiated material, where said irradiated material generates photoacoustic pressure wave signals having peak intensities in response to being irradiated;
   photoacoustic detecting means operably disposed for detecting said photoacoustic pressure wave signals generated by said irradiated material;
   data processor means operably coupled to said photoacoustic detecting means for comparing representations of said peak intensities of said photoacoustic pressure wave signals with a reference value corresponding to a photoacoustic pressure wave signal of one of said material comprising one of said layers of said structure selected to be exposed, and for generating a speed control output signal functionally related to a difference between said peak intensities of said photoacoustic pressure wave signal and said reference value; and
   positioning means operably coupled to receive said speed control output signal from said data processor means for supporting and scanning said radient energy source across said surface.

29. The system of claim 28 wherein said scan speed is functionally related to said difference by a decreasing function, and where said scan speed is a minimum scan speed if said peak intensities of said photoacoustic pressure wave signals peak are equal to or greater than a first threshold value, and said scan speed is a maximum scan speed if said peak intensities of said photoacoustic pressure wave signals are equal to or less than a second threshold value.

30. The system of claim 29 wherein said radient energy source is a broadband flashlamp for generating optical energy.

31. The system of claim 30 wherein said optical energy is modulated at a frequency of 4-5 Hz.

32. The system of claim 31 further including means for cooling said structure with a particle stream to prevent said optical energy beam from substantially changing the modulus of elasticity, shear strength, and tensile strength of said structure.

33. The system of claim 32 wherein said particle stream includes a stream of carbon dioxide pellets entrained in a flowing stream of dry gas directed to impinge said structure.

* * * * *

UNITED STATES PATENT AND TRADEMARK OFFICE
CERTIFICATE OF CORRECTION

PATENT NO. : 5,194,723

DATED : March 16, 1993

INVENTOR(S) : Cates, et al.

It is certified that error appears in the above-identified patent and that said Letters Patent is hereby corrected as shown below:

On the title page, under "Other Publications", under "Klauser", change "(Feb. 1882)" to --(Feb. 1982)--
Column 3, line 58, change "systems" to --system--. Column 5, line 39, after "formed", insert --from--. Column 5, line 40, after "on", insert --a--. Column 5, line 44, change "signals" to --signal--. Column 5, line 67, after "control" delete "o". Column 8, lines 66-67, after "incorporate", insert --the minimum scan rate with a margin of safety. By way of--. Column 10, lines 21-22, change "stantions" to --stations--. Column 12, line 17, change "millivolts,and" to --millivolts, and--. Column 12, line 39, delete "." (period). Column 13, line 3, change "seconds" to --second--. Column 13, line 8, after "millisecond", delete the space. Column 14, line 13, after "robotic", insert --positioner 28--. Column 14, line 35, change "disable" to --disables--. Column 16, line 26, change "prgressively" to --progressively--.
IN THE CLAIMS: In Claim 11, column 18, line 8, after "system", insert --.-- (period).

Signed and Sealed this

First Day of February, 1994

Attest:

BRUCE LEHMAN

*Attesting Officer*   Commissioner of Patents and Trademarks